US010881782B2

(12) United States Patent
Behrens

(10) Patent No.: US 10,881,782 B2
(45) Date of Patent: Jan. 5, 2021

(54) INTRAVENOUS TUBE HOLDING ASSEMBLY

(71) Applicant: David Behrens, Paramus, NJ (US)

(72) Inventor: David Behrens, Paramus, NJ (US)

(*) Notice: Subject to any disclaimer, the term of this patent is extended or adjusted under 35 U.S.C. 154(b) by 182 days.

(21) Appl. No.: 16/156,793

(22) Filed: Oct. 10, 2018

(65) Prior Publication Data

US 2020/0114067 A1 Apr. 16, 2020

(51) Int. Cl.
*A61M 5/14* (2006.01)
*F16L 3/223* (2006.01)
*F16L 3/20* (2006.01)
*F16L 3/13* (2006.01)

(52) U.S. Cl.
CPC ............ *A61M 5/1418* (2013.01); *F16L 3/13* (2013.01); *F16L 3/20* (2013.01); *F16L 3/2235* (2013.01)

(58) Field of Classification Search
CPC . A61M 5/1418; F16L 3/13; F16L 3/20; F16L 3/2235; B60C 27/10; B60C 27/12; Y10S 24/909; A45F 5/004; B60R 22/34; A01K 89/00
USPC ..... 248/68.1, 70, 69; 242/371, 378.1, 378.3; 224/162; 73/760, 761, 796, 789
See application file for complete search history.

(56) References Cited

U.S. PATENT DOCUMENTS

| | | | | |
|---|---|---|---|---|
| 15,440 A * | 7/1856 | Ruggles | ............... | G08B 13/149 116/84 |
| 175,446 A * | 3/1876 | Francis | ................... | B60R 22/34 242/379 |
| 180,327 A * | 7/1876 | Craine et al. | ........... | B60R 22/34 242/379 |
| 245,257 A * | 8/1881 | Wright | .................... | B60R 22/34 242/379 |
| 416,255 A * | 12/1889 | Corthell | ............. | B60R 22/3408 242/378.3 |
| 613,841 A * | 11/1898 | Lord | ........................ | A47G 1/24 248/492 |
| 727,150 A * | 5/1903 | Keller | ................. | B60R 22/3408 242/378.3 |
| 898,083 A * | 9/1908 | Amstalden | .......... | B60R 22/3408 242/378.3 |
| 915,288 A * | 3/1909 | Hagstrom | ........... | B60R 22/3408 242/378.3 |

(Continued)

FOREIGN PATENT DOCUMENTS

| GB | 184228 A * | 8/1922 | ............. A45F 5/004 |
|---|---|---|---|
| KR | 1853309 B1 * | 4/2018 | |

(Continued)

*Primary Examiner* — Kimberly T Wood

(57) ABSTRACT

An intravenous tube holding assembly for organizing and protecting a plurality of intravenous tubes includes a tensioner is removably coupled to an intravenous tube pole. The tensioner is biased in a first direction and the tensioner is urgeable in a second direction. A retainer is provided that has a plurality of engaging slots therein. Each of the engaging slots engages a respective one of a plurality of intravenous tubes for organizing the intravenous tubes. A fastener is provided and the fastener is coupled to the retainer. The fastener releasably engages the tensioner such that the tensioner accommodates a weight of the intravenous tubes in the retainer. Moreover, the tensioner is urged in the second direction when the intravenous tubes are tugged upon.

6 Claims, 4 Drawing Sheets

(56) References Cited

U.S. PATENT DOCUMENTS

| | | | | |
|---|---|---|---|---|
| 1,451,802 A * | 4/1923 | Andrews | A45C 11/323 | 70/456 R |
| 2,732,148 A * | 1/1956 | Lummis | A44B 15/00 | 242/379.2 |
| 2,878,981 A * | 3/1959 | Guido | A62B 35/0093 | 441/80 |
| 4,081,152 A * | 3/1978 | Henderson | B60R 22/44 | 242/371 |
| 4,666,111 A * | 5/1987 | Schuler | A61M 5/1415 | 248/125.1 |
| 5,230,117 A * | 7/1993 | Johnson | A45F 5/004 | 15/106 |
| 5,334,186 A | 8/1994 | Alexander | | |
| 5,336,179 A * | 8/1994 | Ryan | A61M 5/1418 | 128/DIG. 26 |
| 5,389,082 A | 2/1995 | Baugues | | |
| 5,507,460 A * | 4/1996 | Schneider | A61M 5/1418 | 24/601.2 |
| 5,540,468 A * | 7/1996 | Fassman | B65H 75/48 | 224/162 |
| 5,625,855 A * | 4/1997 | Takatori | G03B 17/30 | 396/513 |
| D391,636 S | 3/1998 | Zwerk | | |
| 5,855,262 A * | 1/1999 | Jackson | H02G 11/02 | 191/12.4 |
| 5,938,137 A * | 8/1999 | Poulson | A45F 5/004 | 242/379.2 |
| 6,112,357 A * | 9/2000 | Halloran | A46B 17/02 | 15/106 |
| 6,224,026 B1 * | 5/2001 | Dubois | F16M 11/041 | 248/118.3 |
| 6,257,469 B1 * | 7/2001 | Cohn | A45F 5/004 | 206/86 |
| 6,811,541 B2 * | 11/2004 | Lambert | A61F 5/04 | 602/32 |
| 6,866,128 B2 * | 3/2005 | Moore | H01R 13/60 | 191/12.4 |
| 7,320,681 B2 * | 1/2008 | Gillis | A61M 25/02 | 128/DIG. 26 |
| 7,661,620 B2 * | 2/2010 | Fields | A45F 5/004 | 224/162 |
| 7,805,849 B1 * | 10/2010 | Baker, Jr. | G01C 9/34 | 33/1 LE |
| 9,808,573 B1 * | 11/2017 | Dooley | A61B 50/33 | |
| 9,878,088 B2 * | 1/2018 | Mellard | B01D 71/62 | |
| 10,016,009 B1 * | 7/2018 | Bacchus | A42B 7/00 | |
| 10,413,805 B2 * | 9/2019 | James | A63C 11/00 | |
| 2001/0049504 A1 * | 12/2001 | Gautsche | A61B 46/23 | 604/174 |
| 2002/0000455 A1 * | 1/2002 | Condliff | A45F 5/004 | 224/162 |
| 2002/0096600 A1 | 7/2002 | Cedarberg | | |
| 2005/0072819 A1 * | 4/2005 | Maldonado | A45F 5/021 | 224/162 |
| 2005/0077436 A1 | 4/2005 | Nelson | | |
| 2005/0252939 A1 * | 11/2005 | Schuck | A45F 5/004 | 224/162 |
| 2006/0113432 A1 | 6/2006 | Driskell | | |
| 2007/0051842 A1 * | 3/2007 | Pryor | A45C 11/182 | 242/378.3 |
| 2007/0187555 A1 * | 8/2007 | Rabanin | F16L 3/085 | 248/49 |
| 2008/0042000 A1 * | 2/2008 | Horton | A45F 5/004 | 242/382 |
| 2008/0072849 A1 * | 3/2008 | Henderson | A01K 27/00 | 119/792 |
| 2008/0134554 A1 * | 6/2008 | Pitcher | G09F 7/18 | 40/606.14 |
| 2009/0084479 A1 * | 4/2009 | McCauley | B60C 27/10 | 152/219 |
| 2010/0122560 A1 * | 5/2010 | Ricker | E05B 73/0005 | 70/66 |
| 2010/0294271 A1 * | 11/2010 | Pittaway | A61M 5/1418 | 128/202.13 |
| 2010/0326371 A1 * | 12/2010 | Lopusnak | A01K 27/004 | 119/796 |
| 2011/0174852 A1 * | 7/2011 | Young | A45F 5/02 | 224/268 |
| 2011/0226823 A1 * | 9/2011 | Jasa | A45F 5/004 | 224/162 |
| 2013/0320156 A1 * | 12/2013 | Waldner | B60R 16/0215 | 248/68.1 |
| 2014/0117170 A1 | 5/2014 | Sharpe | | |
| 2014/0306070 A1 * | 10/2014 | Hartsock | A61M 5/1418 | 248/68.1 |
| 2015/0288409 A1 * | 10/2015 | Forsythe | H04B 1/385 | 455/575.6 |
| 2015/0297826 A1 * | 10/2015 | Slaker | A61M 5/1418 | 248/560 |
| 2017/0095066 A1 * | 4/2017 | Martel | A45F 5/004 | |
| 2020/0154869 A1 * | 5/2020 | Jenkins | H04B 1/3888 | |

FOREIGN PATENT DOCUMENTS

| | | | | |
|---|---|---|---|---|
| WO | WO-9732501 A1 * | 9/1997 | | B65H 75/406 |
| WO | WO-2005051462 A1 * | 6/2005 | | A61M 5/1418 |

* cited by examiner

INTRAVENOUS TUBE HOLDING ASSEMBLY

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to holding devices and more particularly pertains to a new holding device for organizing and protecting a plurality of intravenous tubes.

BRIEF SUMMARY OF THE INVENTION

An embodiment of the disclosure meets the needs presented above by generally comprising a tensioner is removably coupled to an intravenous tube pole. The tensioner is biased in a first direction and the tensioner is urgeable in a second direction. A retainer is provided that has a plurality of engaging slots therein. Each of the engaging slots engages a respective one of a plurality of intravenous tubes for organizing the intravenous tubes. A fastener is provided and the fastener is coupled to the retainer. The fastener releasably engages the tensioner such that the tensioner accommodates a weight of the intravenous tubes in the retainer. Moreover, the tensioner is urged in the second direction when the intravenous tubes are tugged upon.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
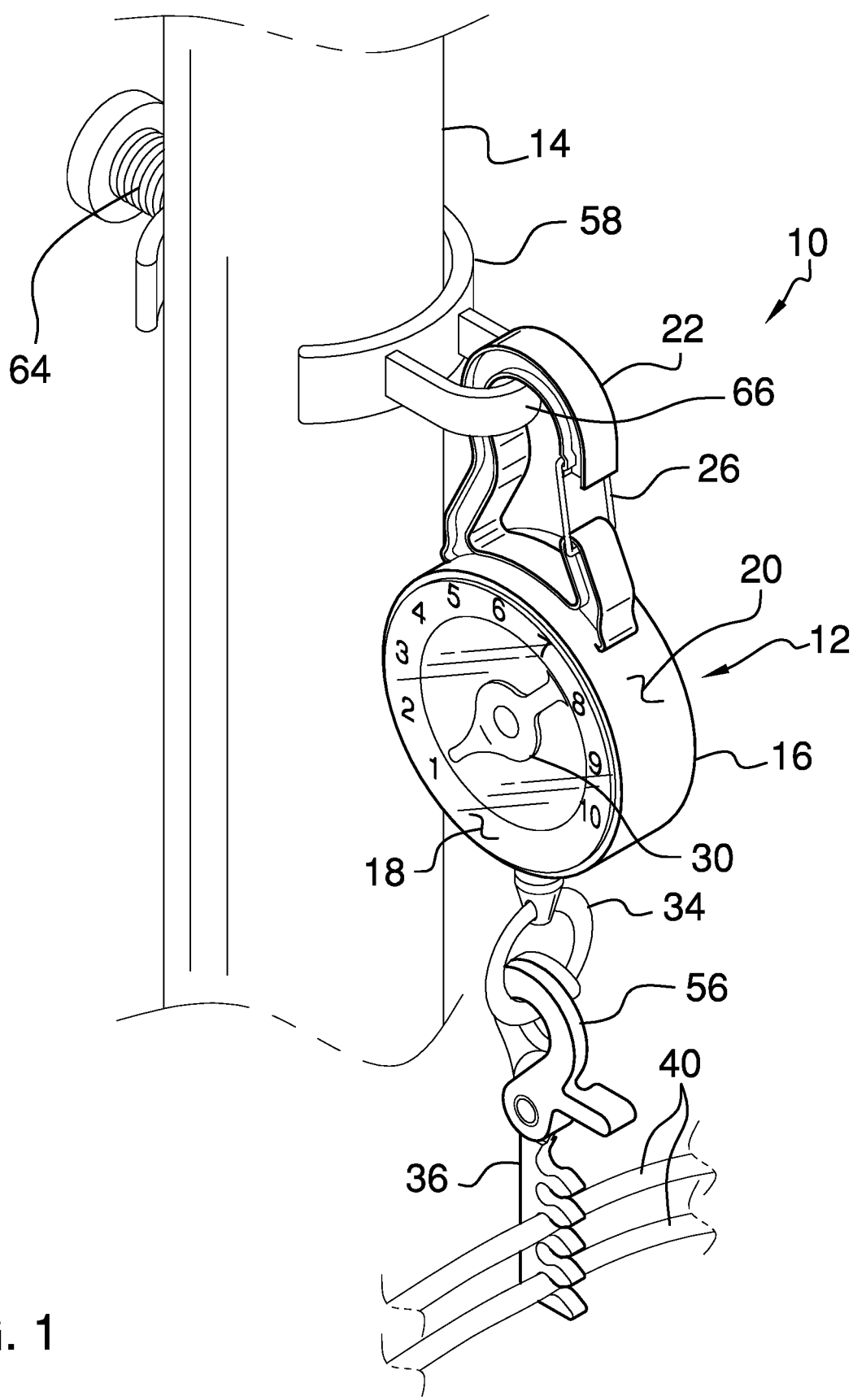
FIG. 1 is a perspective in-use view of an intravenous tube holding assembly according to an embodiment of the disclosure.
Figure 2:
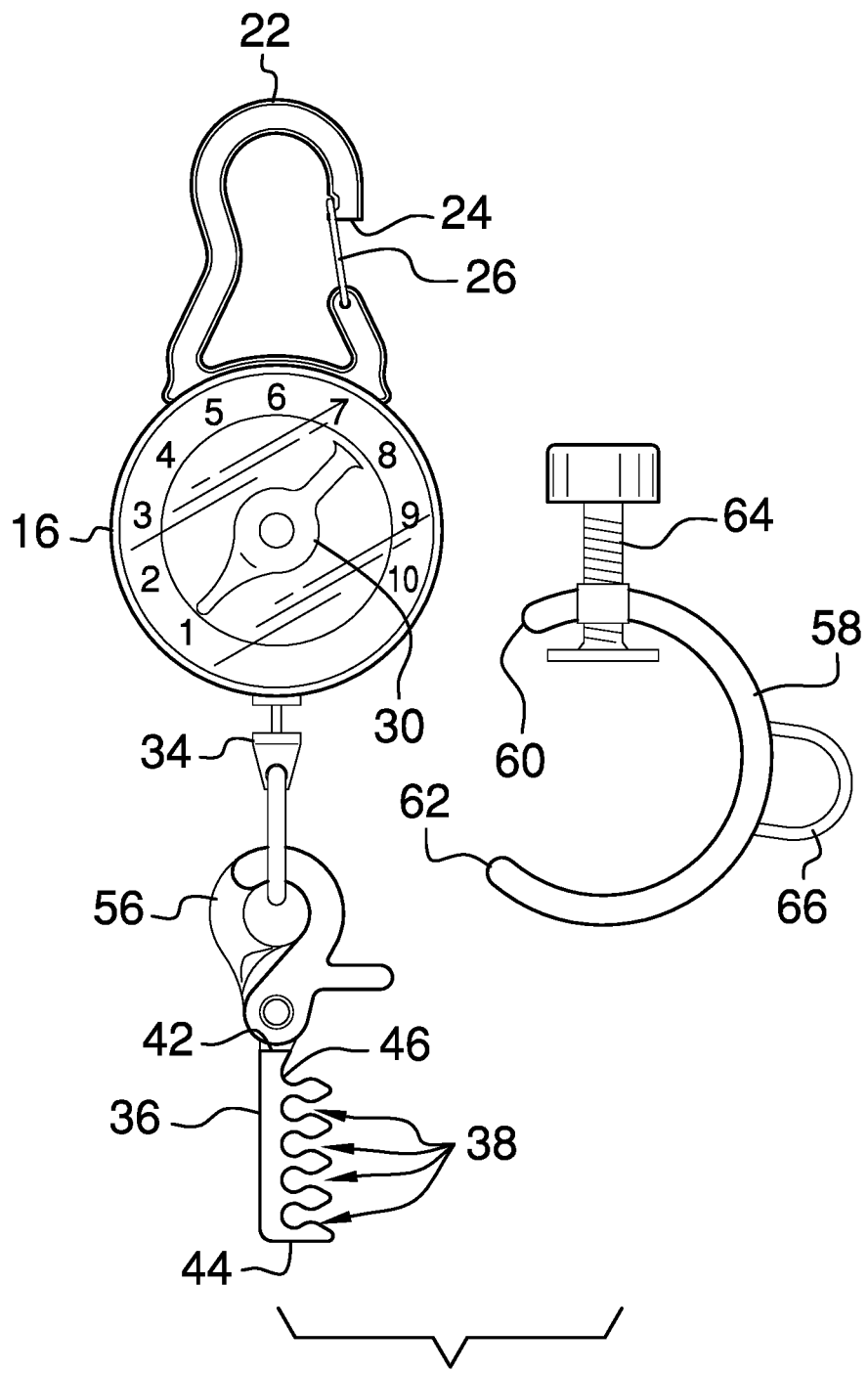
FIG. 2 is a front view of an embodiment of the disclosure.
Figure 3:
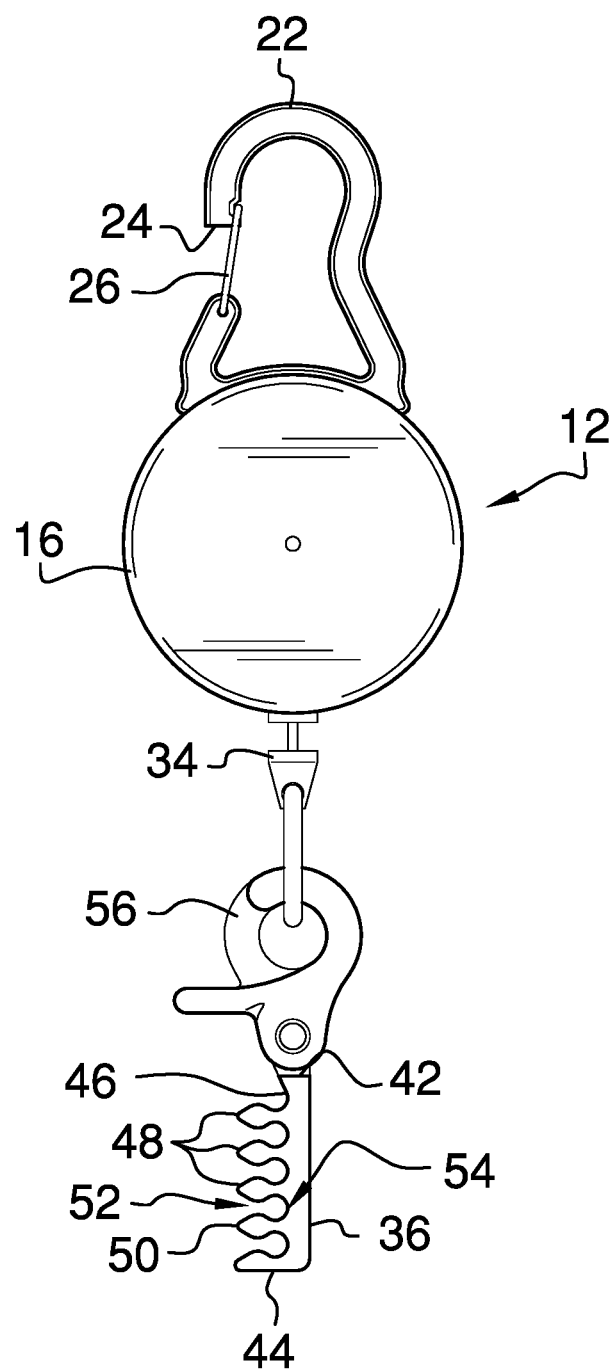
FIG. 3 is a back view of an embodiment of the disclosure.
Figure 4:
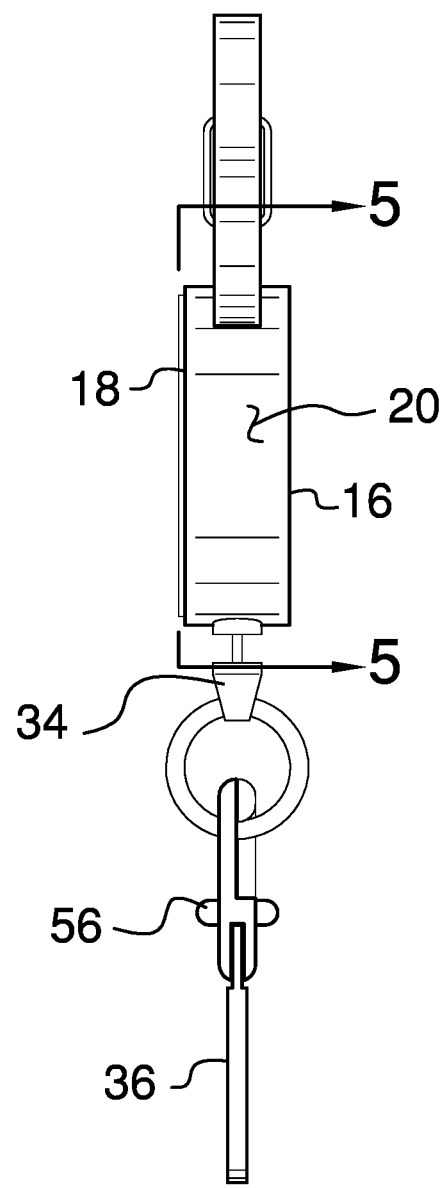
FIG. 4 is a right side view of an embodiment of the disclosure.
Figure 5:
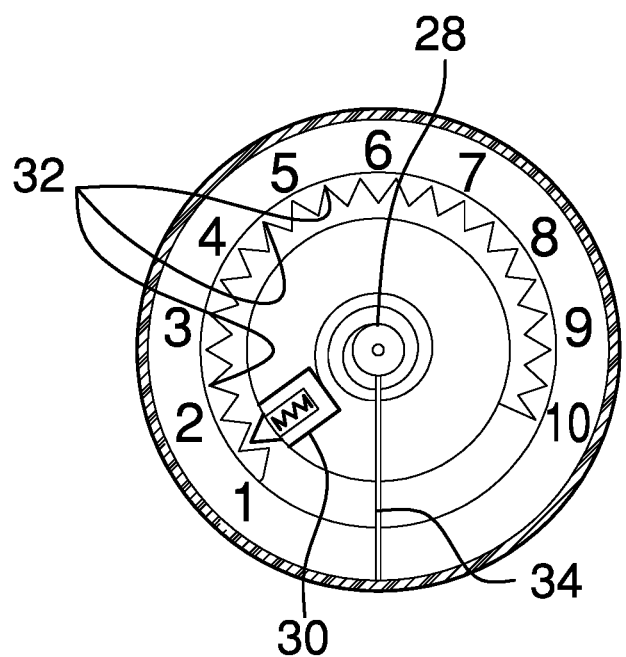
FIG. 5 is a cross sectional view taken along line 5-5 of FIG. 4 of an embodiment of the disclosure.

With reference now to the drawings, and in particular to FIGS. 1 through 5 thereof, a new holding device embodying the principles and concepts of an embodiment of the disclosure and generally designated by the reference numeral 10 will be described.

As best illustrated in FIGS. 1 through 5, the intravenous tube holding assembly 10 generally comprises a tensioner 12 that is removably coupled to an intravenous tube pole 14. The intravenous tube pole 14 may be an intravenous tube pole 14 employed in a medical environment or the like. The tensioner 12 is biased in a first direction and the tensioner 12 is urgeable in a second direction. The tensioner 12 comprises a housing 16 that has a front surface 18 and an outer surface 20, and the outer surface 20 is continuously arcuate such that the housing 16 has a disk shape.

A hook 22 is coupled to and extends away from the outer surface 20 of the housing 16 and the hook 22 has a distal end 24 with respect to the outer surface 20. The hook 22 is curved between the outer surface 20 and the distal end 24 thereby facilitating the hook 22 to engage a support on the intravenous tube pole 14. A closure 26 is pivotally coupled to the outer surface 20 of the housing 16. The closure 26 is biased to engage the distal end 24 of the hook 22 for retaining the hook 22 on the support on the intravenous tube pole 14. Moreover, the closure 26 is spaceable from the distal end 24 of the hook 22 for removing the hook 22 from the support on the intravenous tube pole 14.

The tensioner 12 includes a spool 28 is rotatably positioned within the housing 16. The spool 28 is rotatable in a first direction and a second direction, and the spool 28 is biased to rotate in the first direction. Moreover, the biasing of the spool 28 is adjustable to impart a selected amount of resistance to the spool 28 being rotated in the second direction. The spool 28 may be a spring loaded spool 28 or the like.

A knob 30 is rotatably coupled to the front surface 18 of the housing 16 and the knob 30 engages the spool 28 for adjusting the spool 28 to the selected amount of resistance. The knob 30 releasably engages a selected one of a plurality of detents 32 in the housing 16. Each of the detents 32 is associated with a predetermined amount of resistance to the spool 28 being rotated in the second direction between a minimum amount of resistance and a maximum amount of resistance. The minimum amount of resistance may be an amount of force equal to approximately 56.0 grams of pulling force and the maximum amount of resistance may be an amount of force equal to approximately 450.0 grams of pulling force.

An engagement 34 is movably coupled to the outer surface 20 of the housing 16 such that the engagement 34 is urgeable downwardly away from the housing 16. The engagement 34 is coupled to the spool 28 and the engagement 34 is drawn toward the housing 16 when the spool 28 rotates in the first direction. Additionally, the engagement 34 is moved away from the housing 16 when the spool 28 rotates in the second direction. The engagement 34 may include a cable that is wrapped around the spool 28 and a ring that is coupled to a distal end of the cable.

A retainer 36 is provided that has a plurality of engaging slots 38 therein for engaging a respective one of a plurality of intravenous tubes 40 to organize the intravenous tubes 40. The retainer 36 has a first end 42, a second end 44 and a first surface 46 extending therebetween. The retainer 36 includes a plurality of fingers 48 that each extends laterally away from the first surface 46. Moreover, the fingers 48 are spaced apart from each other and are distributed between the first 42 and second 44 ends of the retainer 36 to define each of the engaging slots 38 between the fingers 48.

Each of the fingers 48 has a distal end 50 with respect to the first surface 46 and each of the fingers 48 is rounded adjacent to the distal end 50 of the fingers 48. Thus, an entrance 52 into each of the engaging slots 38 has a width that is less than a width of a terminus 54 of each of the engaging slots 38. In this way each of the intravenous tubes 40 is frictionally retained in the respective engaging slot 34. The retainer 36 may be comprised of a resiliently compressible material such as rubber or the like.

A fastener 56 is coupled to the retainer 36 and the fastener 56 releasably engages the tensioner 12. Thus, the tensioner 12 can accommodate a weight of the intravenous tubes 40 in the retainer 36. Moreover, the tensioner 12 facilitates the intravenous tubes 40 to be drawn away from the intravenous tube pole 14 without damaging the intravenous tubes 40 when the intravenous tubes 40 are tugged upon or when the intravenous tubes 40 become tangled on an object. The fastener 56 is pivotally coupled to the first end 42 of the retainer 36. The fastener 56 is positionable in an open position for engaging and disengaging the engagement 34 on the tensioner 12. Alternatively, the fastener 56 is positionable in a closed position for retaining the engagement 34 on the tensioner 12. The fastener 56 may comprise a lobster claw clip or other mechanically releasable fastener.

A clamp 58 is provided that releasably attaches to the intravenous tube pole 14. The clamp 58 has a first end 60 and a second end 62, and the clamp 58 is concavely arcuate between the first 60 and second 62 ends of the clamp 58. Thus, the clamp 58 can be positioned around the intravenous tube pole 14. A screw 64 is rotatably coupled to the clamp 58 and the screw 64 engages the intravenous tube pole 14 when the screw 64 is tightened to retain the clamp 64 on the intravenous tube pole 14. A loop 66 is coupled to the clamp 58 and the hook 22 on the tensioner 12 releasably engages the loop 66 for suspending the tensioner 12 from the clamp 64.

In use, the hook 22 on the tensioner 12 is coupled to the support on the intravenous tube pole 14 and a selected number of intravenous tubes 40 is positioned in the engaging slots 38 in the retainer 36. The knob 30 on the tensioner 12 is manipulated to select an amount of resistance that corresponds to the number of intravenous tubes 40 positioned in the retainer 36. In this way the tensioner 12 simultaneously supports the weight of the intravenous tubes 40 and facilitates the intravenous tubes 40 to be drawn away from the tensioner 12 when the intravenous tube are tugged upon. Thus, the tensioner 12 inhibits the intravenous tubes 40 from being damaged from tugging and the tensioner 12 further inhibits the intravenous tubes 40 from lying on the floor. In this way the tensioner 12 and the retainer 36 organize the intravenous tubes 40 and inhibit the intravenous tubes 40 from being damaged. Thus, a plurality of intravenous medications can be safely delivered to a patient without the risk of tangling the intravenous tube or inadvertently pulling the intravenous tubes 40 out of the patient.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An intravenous tube holding assembly being configured to organize a plurality of intravenous tubes being used on a patient, said assembly comprising:

a tensioner being removably coupled to an intravenous tube pole, said tensioner being biased in a first direction, said tensioner being urgeable in a second direction;

a retainer having a plurality of engaging slots therein for engaging a respective one of a plurality of intravenous tubes wherein said retainer is configured to organize the intravenous tubes; and a fastener being coupled to said retainer, said fastener releasably engaging said tensioner wherein said tensioner is configured to accommodate a weight of the intravenous tubes in said retainer, said tensioner being urged in said second direction when the intravenous tubes are tugged upon; and wherein said tensioner comprises a housing having a front surface and an outer surface, said outer surface being continuously arcuate such that said housing has a disk shape, a hook being coupled to and extending away from said outer surface, said hook having a distal end with respect to said outer surface, said hook being curved between said outer surface and said distal end thereby facilitating said hook to engage a support on the intravenous tube pole, a closure being pivotally coupled to said outer surface of said housing, said closure being biased to engage said distal end of said hook for retaining said hook on the support on the intravenous tube pole, said closure being spaceable from said distal end of said hook for removing said hook from the support on the intravenous tube pole, a spool being rotatably positioned within said housing, said spool being rotatable in the first direction and the second direction, spool being biased to rotate in said first direction, said biasing of spool being adjustable to impart a selected amount of resistance to said spool being rotated in said second direction, and a knob being rotatably coupled to said front surface of said housing, said knob engaging said spool for adjusting said spool to said selected amount of resistance, said knob releasably engaging a selected one of a plurality of detents in said housing, each of said detents being associated with a predetermined amount of resistance to said spool being rotated in said second direction between a minimum amount of resistance and a maximum amount of resistance.

2. The assembly according to claim 1, wherein said tensioner comprises an engagement being movably coupled to said outer surface of said housing such that said engagement is urgeable downwardly away from said housing, said engagement being coupled to said spool, said engagement being drawn toward said housing when said spool rotates in said first direction, said engagement being moved away from said housing when said spool rotates in said second direction.

3. The assembly according to claim 1, wherein said retainer has a first end, a second end and a first surface extending therebetween, said retainer including a plurality of fingers each extending laterally away from said first surface, said fingers being spaced apart from each other and being distributed between said first and second ends of said retainer to define each of said engaging slots between said fingers, each of said fingers having a distal end with respect to said first surface.

4. The assembly according to claim 3, wherein each of said fingers is rounded adjacent to said distal end such that an entrance into each of said engaging slots has a width being less than a width of a terminus of each of said engaging slots thereby frictionally retaining each of the intravenous tubes in said respective engagement slot.

5. The assembly according to claim 3, wherein said fastener is pivotally coupled to said first end of said retainer, said fastener being positionable in an open position for engaging and disengaging an engagement on said tensioner, said fastener being positionable in a closed position for retaining said engagement on said tensioner.

6. An intravenous tube holding assembly being configured to organize a plurality of intravenous tubes being used on a patient, said assembly comprising:

a tensioner being removably coupled to an intravenous tube pole, said tensioner being biased in a first direction, said tensioner being urgeable in a second direction, said tensioner comprising:

a housing having a front surface and an outer surface, said outer surface being continuously arcuate such that said housing has a disk shape;

a hook being coupled to and extending away from said outer surface, said hook having a distal end with respect to said outer surface, said hook being curved between said outer surface and said distal end thereby facilitating said hook to engage a support on the intravenous tube pole;

a closure being pivotally coupled to said outer surface of said housing, said closure being biased to engage said distal end of said hook for retaining said hook on the support on the intravenous tube pole, said closure being spaceable from said distal end of said hook for removing said hook from the support on the intravenous tube pole;

a spool being rotatably positioned within said housing, said spool being rotatable in the first direction and the second direction, spool being biased to rotate in said first direction, said biasing of spool being adjustable to impart a selected amount of resistance to said spool being rotated in said second direction;

a knob being rotatably coupled to said front surface of said housing, said knob engaging said spool for adjusting said spool to said selected amount of resistance, said knob releasably engaging a selected one of a plurality of detents in said housing, each of said detents being associated with a predetermined amount of resistance to said spool being rotated in said second direction between a minimum amount of resistance and a maximum amount of resistance; and an engagement being movably coupled to said outer surface of said housing such that said engagement is urgeable downwardly away from said housing, said engagement being coupled to said spool, said engagement being drawn toward said housing when said spool rotates in said first direction, said engagement being moved away from said housing when said spool rotates in said second direction;

a retainer having a plurality of engaging slots therein for engaging a respective one of a plurality of intravenous tubes wherein said retainer is configured to organize the intravenous tubes, said retainer having a first end, a second end and a first surface extending therebetween, said retainer including a plurality of fingers each extending laterally away from said first surface, said fingers being spaced apart from each other and being distributed between said first and second ends of said retainer to define each of said engaging slots between said fingers, each of said fingers having a distal end with respect to said first surface, each of said fingers being rounded adjacent to said distal end such that an entrance into each of said engaging slots has a width being less than a width of a terminus of each of said engaging slots thereby frictionally retaining each of the intravenous tubes in said respective engagement slot;

a fastener being coupled to said retainer, said fastener releasably engaging said tensioner wherein said tensioner is configured to accommodate a weight of the intravenous tubes in said retainer, said fastener being pivotally coupled to said first end of said retainer, said fastener being positionable in an open position for engaging and disengaging said engagement on said tensioner, said fastener being positionable in a closed position for retaining said engagement on said tensioner.

* * * * *